(12) United States Patent
Kruzel et al.

(10) Patent No.: US 7,691,809 B2
(45) Date of Patent: Apr. 6, 2010

(54) LACTOFERRIN FOR AGE RELATED DISORDERS IN HUMANS

(75) Inventors: Marian L. Kruzel, Houston, TX (US); Tadeusz Kruzel, Legnica (PL); Michal Zimecki, Wroclaw (PL)

(73) Assignee: Vitaerx Pharmaceutical, Inc., Pearland, TX (US)

( * ) Notice: Subject to any disclaimer, the term of this patent is extended or adjusted under 35 U.S.C. 154(b) by 1438 days.

(21) Appl. No.: 11/040,963

(22) Filed: Jan. 22, 2005

(65) Prior Publication Data

US 2005/0159340 A1 Jul. 21, 2005

Related U.S. Application Data

(63) Continuation-in-part of application No. 10/140,380, filed on May 7, 2002, now abandoned.

(60) Provisional application No. 60/289,666, filed on May 9, 2001.

(51) Int. Cl.
*A61K 38/00* (2006.01)
*A61K 38/16* (2006.01)

(52) U.S. Cl. .................. 514/6; 514/2; 514/8; 514/12

(58) Field of Classification Search ............ 514/2, 514/6, 8, 12
See application file for complete search history.

(56) References Cited

U.S. PATENT DOCUMENTS

| | | | |
|---|---|---|---|
| 4,136,160 A * | 1/1979 | Cohen | 424/1.57 |
| 4,977,137 A | 12/1990 | Nichols et al. | |
| 5,066,491 A | 11/1991 | Stott et al. | |
| 5,240,909 A | 8/1993 | Nitsche | |
| 5,531,989 A | 7/1996 | Paul | |

OTHER PUBLICATIONS

Penco et al. "Lactoferrin Down-modulates the ACtivity of the Granulocyte Macrophage Colony-stimulating Factor Promoter in interleukin-1b-stimulated Cells" The Journal of Biological Chemistry, 1995, vol. 270, No. 20, Issue of May 19, pp. 12263-12268.*
Sanches L. et al, Biological Role of Lactoferrin; Arch. Dis. Child; 1992; 67:657-661.
Lonnerdal, B. et al: Lactoferrin: Molecular Structure and Biological Function; Annu. Rev. Nutr. 15, 1995; 93-110.
Zagulski, T., et al.: Lactoferrin can protect mice against a lethal dose of *Escherichia coli* in experimental infection in vivo; Br J Exp Pathol; 1989; 70:697-704.
Brock, J.H.; Lactoferrin in human milk; its role in iron absorption and protection against enteric infection in the newborn infants; Arch. Dis. Child; 1955; 080:417-421.
Howie, P.W. et al; Protective effects of breast feeding; B.M.J. 300; 1990; 11-16.
Zimecki, M. et al.; Lactoferrin inhibits the effector phase of delayed type hypersensitivy to sheep erythrocytes and inflammatory reactions to M. bovis; Arch Immunol Ther Exp; 42; 1994; 171-177.

Zimecki, M. et al.; Human lactoferrin induces phenotypic and functional changes in splenic mouse B cells; Immunology 1995; 86: 112-127.
Kruzel, M. et al; Lactoferrin protects gut mucosal integrity during endotoxemia induced by lipopolysaccharide in mice; Inflammation 2000; vol. 24; No. 1; 33-44.
Zimecki, M. et al; Regulatory effects of lactoferrin and lipopolysaccharide on LFA-1 expression on human peripheral blood mononuclear cells; Arch Immunol Ther Exp; 1999; 47:257-264.
Bayens, RD., at al; Lactoferrin and the inflammatory response in: Lactoferrin: Structure and Function, eds. T.W. Hutchens et al., Plenum Press, 1994; 133-141.
Touyz, R.M.; Oxidative stress and vascular damage in hypertension; Curr Hypertens Rep.; 2000; 2(1): 98-105.
Halliwell, B., Reactive oxygen species and the central nervous system; J. Neurochem; 1992; 59(5): 1609-23.
Gutteridge JMC; Hydroxyl radicals, iron, oxidative stress, and neurodegeneration; Ann N Y Acad Sci.; 1994; 738:201-13.
Ebadi, M. et al.; Oxidative stress and antioxidant therapy in Parkinson's disease; Prog Neurobiol; 1996; 48: 1-19.
Markesbery, W.R., et al; Oxidative alterations in Alzheimer's disease; Brain Pathol; 1999; 9:133-46.
Behl, C.; Vitamin E and other antioxidants in neuroprotection; Int J Vitam Nutr Res. 1999; 69:213-219.
Olanow, C.W. et al; Metals and free radicals in neurodegeneration; Curr Opin Neurol; 1994; 7(6):548-58.
Coyle, et al; Oxidative stress, glutamate, and neurodegenerative disorders; Science 1993; 262 (5134); 689-95.
Facchinetti, F., et al; Free radicals as mediators of neuronal injury; 1998; 18(6): 667-82.
Kovacic, P., et al; Mechanisms of carcinogenesis: focus on oxidative stress and electron transfer, 2001; 8(7): 773-96).
Britigan B.E.; et al; The role of lactoferrin as an anti-inflammatory molecule; Lactoferrin: Structure and Function; 1994; 143-156.
Bayens, RD., et al; Lactoferrin and the inflammatory response in: Lactoferrin: Structure and Function, eds. T.W. Hutchens et al., Plenum Press, 1994; 133-141.
Satue-Gracia M.T., et al; Lactoferrin in infant formulas: effect on oxidation; J Agric Food Chem; 2000; 48(10): 4984-90.
Penco, S., et al; A study of lactoferrin and antibodies against lactoferrin in neurological diseases; Adv Exp Med Biol; 1998; 443: 301-40.
Locht, H. et al; Anti-lactoferrin antibodies and other types of antineurrophil cytoplasmic antibodies (ANCA) in reactive arthritis and ankylosing spondylitis; Clin Exp Immunol; 1999; 117Θ3) 568-73.
Brock, J.; Lactoferrin: a multifunctional immunoregulatory protein: Immunology Today; 1995: 16:417-419.

(Continued)

*Primary Examiner*—Jennifer M Kim
(74) *Attorney, Agent, or Firm*—Conley Rose, P.C.

(57) ABSTRACT

The method of the present invention provides a novel use of lactoferrin to modulate the molecular events during development of age-related disorders in humans. More specifically, the present invention is directed to the use of lactoferrin to treat or prevent autoimmune, neurodegenerative and immune hypersensitivity disorders, and its use for the manufacture of a medicament for the treatment or prevention of such conditions.

7 Claims, 6 Drawing Sheets

OTHER PUBLICATIONS

Simonian, NA; et al; Oxidative stress in Neurodegenerative diseases; Annu Rev Pharmacol Toxicol; 1996; 36: 83-106.

Zimecki, M. et al; Immunoregulatory activities of lactoferrin in the delayed type hypersensitivity in mice are mediated by a receptor with affinity to mannose; Immunobiology: 2002:2005(1):120-31.

Zimecki, M. et al; Lactoferrin regulates proliferative response of human peripheral mononuclear cells to phytohemaagglutinin and mixed lymphocytes reaction: Arch Irrununol. Ther Exp 2001:49:147-154.

Actor, J. et al; Lactoferrin immunomodulation of DTH response in mice; Int Immunopharmacol: 2002:2(4): 475-86.

Frydecka, I. et al; Lactoferrin-induced up-regulation of zeta (zeta) chain expression in peripheral blood T lymphocytes from cervical cancer patients; Anticancer Res. 2002; 22(3):1897-901.

Zimecki, M. et al; Lactoferrin regulates the immune responses in post-surgical patients: Arch Immunol Ther Exp 2001; 49:325-333.

* cited by examiner

| Analysis | |
|---|---|
| | |
| Protein | 91.2% |
| Lipids | Not Detectable |
| Carbohydrates | 3.1% |
| Ash | 0.31% |
| Moisture | 4.2% |

Table 1

| Test | Initiation | 1 month | 2 months |
|---|---|---|---|
|  |  |  |  |
| MMSE | 13 | 19 | 21 |
| Clock Test | -,-,- | -,+,+ | +,+,+ |
| Verbal Confidence Test | k-1;animals-6; sharp objects-5 | k-2;animals-7; sharp objects-7 | k-3;animals-9; sharp objects-9 |
| Learning Curve | 0,5,2,4,4;2 (3);2 | 2,5,3,4,4;3(4)3 | 3,5,3,4,4;3(4)4 |

Table 2

LACTOFERRIN FOR AGE RELATED DISORDERS IN HUMANS

RELATED APPLICATIONS

This application is a continuation in part of U.S. application Ser. No. 10/140,380, filed May 7, 2002, now abandoned entitled "Lactoferrin for age related disorders in humans", which in turn is based on provisional application No. 60/289,666 filed May 9, 2001, entitled "Method for the Use of Lactoferrin to Modulate Immune Responses in Humans and Animals", which are incorporated herein by reference.

FIELD OF THE INVENTION

The present invention is directed to the use of lactoferrin to treat age-related disorders such as autoimmune, neurodegenerative and immune hypersensitivity conditions, including Alzheimer's, Parkinson's, multiple sclerosis, rheumatoid arthritis, cancer, allergy, stroke or fatigue, and its use for the manufacture of a medicament for the treatment or prevention of such disorders in humans. The present invention is based on the observation that exogenous lactoferrin is a useful mediator of immune responses, and in particular, effective in the slowing down of the progression or preventing the development of many debilitating conditions in humans.

BACKGROUND OF THE INVENTION

Lactoferrin, an iron-binding glycoprotein, is considered an important mediator in host defense against pathogenic organism. The significance of lactoferrin in health and disease has been the subject of several reviews (Sanches L., Calvo M., Brock J H., (1992) Biological role of lactoferrin. Arch Dis Child. 67, 657-661; Lonnerdal B., Iyer S. (1995). Lactoferrin: molecular structure and biological function. Annu. Rev. Nutr. 15, 93-110). Lactoferrin has well-defined, direct antimicrobial activity (Zagulski T, Lipinski P, Zagulska A, Broniek S, Jarzabek Z. Lactoferrin can protect mice against a lethal dose of *Escherichia coli* in experimental infection in vivo. Br J Exp Pathol. 1989; 70(6): 697-704). It can also be categorized as an immunomediator during inflammatory responses. Lactoferrin is particularly active at mucosal surfaces. Because of its high concentration in human colostrum, lactoferrin has been studied extensively in host defense responses in infants (Brock J. H. Lactoferrin in human milk: its role in iron absorption and protection against enteric infection in the newborn infants. Arch. Dis. Child. 1980; 55, 417-421; Howie P W., Forsyth J S., Ogston S A., Clark A., du V. Florey C. Protective effects of breast feeding. B. M. J. 1990; 300, 11-16). It is theorized that lactoferrin within human milk provides protection against pathogens during newborn adaptation to non-uterine life, and plays a role in rendering breast-fed infants more resistant to the development of microbe-induced gastroenteritis (compared to formula-fed babies). U.S. Pat. No. 4,977,137 of Nichols et al. discloses milk lactoferrin as a dietary ingredient which promotes growth of the gastrointestinal tract of human infants and newborn nonhuman animals immediately on birth. Nichols discusses the use of lactoferrin in the management of short gut syndrome, an anatomical dysfunction.

Lactoferrin has a profound modulatory action on the immune system (Zimecki M., Machnicki M., Lactoferrin inhibits the effector phase of delayed type hypersensitivity to sheep erythrocytes and inflammatory reactions to *M. bovis* (BCG). Arch Immunol Ther Exp 1994; 42:171-177), it promotes maturation of T cell precursors into immunocompetent helper cells and differentiation of immature B cells to become efficient antigen presenting cells (Zimecki M., Mazurier J., Spik G., Kapp J A. Human lactoferrin induces phenotypic and functional changes in splenic mouse B cells. Immunology 1995; 86:112-127). Lactoferrin is an integral part of the cytokine-induced cascade during insult-induced metabolic imbalance (Kruzel M., Harari Y., Chen Y., Castro A. G. Lactoferrin protects gut mucosal integrity during endotoxemia induced by lipopolysaccharide in mice. Inflammation 2000; 24:33-44). Receptors for Lactoferrin have been identified and characterized on monocytes, B and T cells. Lactoferrin injected intravenously, intraperitoneally, or orally is quickly taken up by cells of the immune system, preferably by cells of the reticuloendothelial-system. Lactoferrin upregulates expression of leukocyte function associated-1 (LFA-1) antigen on human peripheral blood lymphocytes (Zimecki M, Miedzybrodzki R, Mazurier J, Spik G. Regulatory effects of lactoferrin and lipopolysaccharide on LFA-1 expression on human peripheral blood mononuclear cells. Arch Immunol Ther Exp 1999; 47:257-264). As presented in FIG. 1, lactoferrin can modulate the outcomes of acute inflammation, which is fundamentally a protective response to cell injury as disclosed in PCT application number WO 98/50076, entitled "Methods for Preventing and Treating the Insult-Induced Metabolic imbalance in humans and other Animals", filed May 3, 1997, all of which is incorporated herein by reference.

The role of lactoferrin in modulating both the acute and chronic inflammation is under active investigation. By virtue of high affinity to iron lactoferrin is considered an important component of nonspecific host defense system against various pathogens in humans. However, a high level of lactoferrin in plasma has been suggested to be a predictive indicator of sepsis-related morbidity and mortality (Bayens R D., Bezwoda W R. Lactoferrin and the inflammatory response In: Lactoferrin: Structure and Function, eds. T. W. Hutchens et al., Plenum Press, 1994; pp. 133-141). In addition, progression in chronic inflammatory disorders, such as Alzheimer's disease, or autoimmune disorder such, as multiple sclerosis, seems not to be interrupted by lactoferrin elevation in various physiological fluids. Although, the endogenous production of lactoferrin is increased in these disorders, it is either not sufficient, or does not trigger the pathway(s) of molecular events to aid a defense system against the disorder. It is possible that the exogenous lactoferrin, especially when given orally, transduces different signaling pathways than the endogenous lactoferrin molecule. Consequently, the end effects are different.

Under normal physiological conditions, the rate and magnitude of reactive oxidants formation is balanced by the rate of their elimination. An imbalance between reactive oxidants production and antioxidant defense results in oxidative stress, which may lead to the oxidative cell injury (Touyz R M. "Oxidative stress and vascular damage in hypertension". Curr Hypertens Rep. 2000; 2(1): 98-105). Oxidative stress can contribute to many diseases including fatigue, sepsis, autoimmune diseases, cancer, neurodegenerative diseases, heart attack and stroke. Transitional metals have been considered as key factors in the oxidative stress. In particular, traces of iron can be detrimental to physiological processes under reactive oxygen conditions. Iron is in a center of the reactive oxygen species control. It has the ability to catalyze two step process known as the Haber-Weiss reaction (FIG. 2). In the first reaction a superoxide molecule reacts with iron ($3^+$) salt to form iron ($2^+$) salt and ground state oxygen. The second reaction is known as the Fenton reaction. In this reaction iron ($2^+$) salt reacts with hydrogen peroxide to form iron ($3^+$) salt, the hydroxyl radical and alcohol.

In normal physiological conditions the production and neutralization of these reactive oxygen species (ROS) depend on the efficiency of key enzymes, including superoxide dismutase (SOD), catalase (CAT) and glutathione peroxidase (GPX). If the process of neutralization of ROS is not efficient, it can contribute to development of oxidative stress (e.g. lipid peroxidation). Although, endogenous lactoferrin participates in these processes at cellular level it is not understood how exogenous lactoferrin would contribute to these molecular events (FIG. 2). Again, based on the recognition that lactoferrin level increases during development of some autoimmune and neurologic conditions, the use of exogenous lactoferrin would not be scientifically justified.

Reactive oxygen species are capable of catalyzing morphological changes to proteins, in both beneficial and non-beneficial ways. The ability of a cell to control these changes in oxidation and resulting protein effects is very important for species survival. Recently, intermediates in the lipid peroxidation process have shown the ability to inactivate and modify proteins. This is an important finding because proteins in biological membranes may become a primary target in radical-induced cell death. Lipid peroxidation is tentatively defined as the oxidative deterioration of polyunsaturated lipids. These fatty acids provide mobility and fluidity to the plasma membrane, properties which are known to be essential for the proper function of biological membranes. The process of lipid peroxidation is a step-wise process with an initiation and subsequent propagation reactions. Iron and other transitional metals help to initiate the process by forming alkeoxy or peroxy radicals upon reaction with oxygen species. The fatty acids are reduced to reactive aldehydes and hydrocarbons. In general, the damaging consequences of lipid peroxidation are expressed as a decrease in the fluidity of the membrane and subsequent increase in its permeability to substances which normally do not pass.

The nervous system, including the brain, spinal cord, and peripheral nerves, is rich in both unsaturated fats and iron (Halliwell. Reactive oxygen species and the central nervous system. J. Neurochem. 1992; 59(5): 1609-23). The high lipid content of nervous tissue, coupled with its high metabolic activity, makes it particularly susceptible to oxidant damage. The high level of brain iron may be essential to oxidative stress via the iron-catalyzed formation of reactive oxygen species.

In the age related disorders that develop over decades, many chemical species as well as pathophysiological conditions are involved. The major threat comes from the oxidative stress. The generation of the reactive oxygen species can lead to immediate damage or death of cells in various tissues (Gutteridge. Hydroxyl radicals, iron, oxidative stress, and neurodegeneration. Ann N Y Acad. Sci. 1994; 738:201-13). There is substantial evidence that oxidative stress is a causative factor in the pathogenesis of major neurodegenerative diseases, including Parkinson's disease (Ebadi M, Srinivasan S K, Baxi M D. Oxidative stress and antioxidant therapy in Parkinson's disease. Prog Neurobiol. 1996; 48(1):1-19), Alzheimer's disease (Markesbery W R, Carney J M. Oxidative alterations in Alzheimer's disease. Brain Pathol. 1999; 9(1):133-46.; Behl Vitamin E and other antioxidants in neuroprotection. Int J Vitam Nutr Res. 1999; 69(3):213-9), and amyotrophic lateral sclerosis (Olanow and Arendash Metals and free radicals in neurodegeneration. Curr Opin Neurol. 1994; 7(6):548-58.; Simonian and Coyle Oxidative stress in neurodegenerative diseases. Annu Rev Pharmacol Toxicol. 1996; 36:83-106) as well as in cases of stroke, trauma, and seizures (Coyle and Puttfarcken. Oxidative stress, glutamate, and neurodegenerative disorders. Science. 1993; 262(5134): 689-95.; Facchinetti F, Dawson V L, Dawson T M. Free radicals as mediators of neuronal injury. Cell Mol Neurobiol. 1998; 18(6):667-82) or rheumatoid arthritis, fatigue and cancer (Kovacic P, Jacintho J D. Mechanisms of carcinogenesis: focus on oxidative stress and electron transfer. Curr Med Chem 2001; 8(7):773-96).

Also, there is ample evidence that allergic disorders, such as asthma, rhinitis, and atopic dermatitis, are mediated by oxidative stress (Bowler R P., Capro J D. (2002): Oxidative stress in allergic respiratory diseases J Allergy Clin Immunol. 110:349-56). In fact, the oxidative stress-induced immune hypersensitivity indicates a shift in immunostasis towards the Th2 responses. The Th1/Th2 balance is responsible for coordinating the immune system and become very important during aging processes, including the development of autoimmune, neurodegenerative and immune hypersensitivity disorders.

Although, considerable data from in vitro experiments indicate several physiological roles for lactoferrin, there is no firm evidence concerning its actual physiological function from in vivo studies. For example, in a review by Roy D. Byens and Werner R. Bezwoda entitled "Lactoferrin and the inflammatory response" and published in the book: *Lactoferrin: Structure and Function*, pp 133-141, (1994), a relationship between plasma lactoferrin and granulocyte activity in sepsis is mentioned. However, the biological function of the significant amounts of lactoferrin in plasma of septic patients is as yet not completely understood.

Similarly, marked elevation of lactoferrin has been noted in the cerebrospinal fluid of patients with acute cerebrovascular lesions and other pathological lesions in variety of neurodegenerative disorders (Penco S, Villaggio B, Mancardi G, Abbruzzese M, Garre C. A study of lactoferrin and antibodies against lactoferrin in neurological diseases. Adv Exp Med Biol. 1998; 443:301-40). Based on this observation the use of exogenous lactoferrin in patients who overexpress its own lactoferrin would not be scientifically justified.

In another review entitled "*The role of lactoferrin as an anti-inflammatory molecule*" by Bradley E. Britigan, Jonathan S. Serody, and Myron S. Cohen and published in the book: *Lactoferrin: Structure and Function*, pp 143-156, (1994), the role of lactoferrin in inflammation is suggested to be played at two different levels: (i) as an antioxidant, capable of binding free iron, and (ii) as an endotoxin scavenger, capable of reducing lipopolysaccharide (LPS)-induced toxicity.

In yet another article entitled "Lactoferrin in infant formulas: effect on oxidation", by Satue-Gracia M T, Frankel E N, Rangavajhyala N, German J B., and published in J Agric Food Chem. 2000; 48(10):4984-90, authors emphasize the ability of lactoferrin to control oxidation in infant formulas.

Relevant patents are also silent as to the use of lactoferrin for prevention or therapy of autoimmune or neurodegenerative disorders in humans and animals. U.S. Pat. No. 5,240,909 of Nitsche relates to the use of lactoferrin as an agent for the prophylactic and therapeutic treatment of the toxic effects of endotoxins. Nitche discloses that the lactoferrin used according to his invention has the ability to neutralize endotoxin and must have bound to it either iron or another metal to be effective. U.S. Pat. No. 5,066,491 of Stott et al. encompasses a method of disease treatment utilizing a therapeutically effective product produced from ordinary milk whey.

Despite large number of studies on lactoferrin, there is no disclosure that it can function as a mediator to reduce the debilitating conditions in the autoimmune, neurodegenerative and immune hypersensitivity disorders such as Alzheimers, Parkinson's, multiple sclerosis, rheumatoid arthritis, cancer, allergy, stroke or fatigue. The knowledge about endogenous lactoferrin is not supporting the clinical effects of exogenous lactoferrin as found in the present invention. For example, autoantibodies to lactoferrin are commonly found in many autoimmune disorders, including multiple sclerosis (Penco S, Villaggio B, Mancardi G, Abbruzzese M, Garre C. A study of lactoferrin and antibodies against lactoferrin in neurological diseases. Adv Exp Med Biol. 1998; 443:301-40) and rheumatoid arthritis (Locht H, Skogh T, Kihlstrom E. Anti-lactoferrin antibodies and other types of anti-neutrophil cytoplasmic antibodies (ANCA) in reactive arthritis and ankylosing spondylitis. Clin Exp Immunol. 1999; 117(3):568-73). In fact, the presence of these antibodies has been suggested to be used as marker for the inflammatory disorders. Based on this observation the use of lactoferrin in patients with autoantibodies to lactoferrin would not be scientifically justified. According to present invention, exogenous lactoferrin has been found to reduce the symptoms of autoimmune, neurodegenerative and immune hypersensitivity disorders.

SUMMARY OF THE INVENTION

The method of the present invention provides a novel use of lactoferrin to modulate the molecular events during development of age related disorders including autoimmune, neurodegenerative and immune hypersensitivity disorders in humans. More specifically, the present invention is directed to the use of lactoferrin to treat or prevent age related disorders such as Alzheimer's disease, multiple sclerosis, rheumatoid arthritis, allergy, stroke or chronic fatigue syndrome, and its use for the manufacture of a medicament for the treatment or prevention of such disorders.

Figure 1:
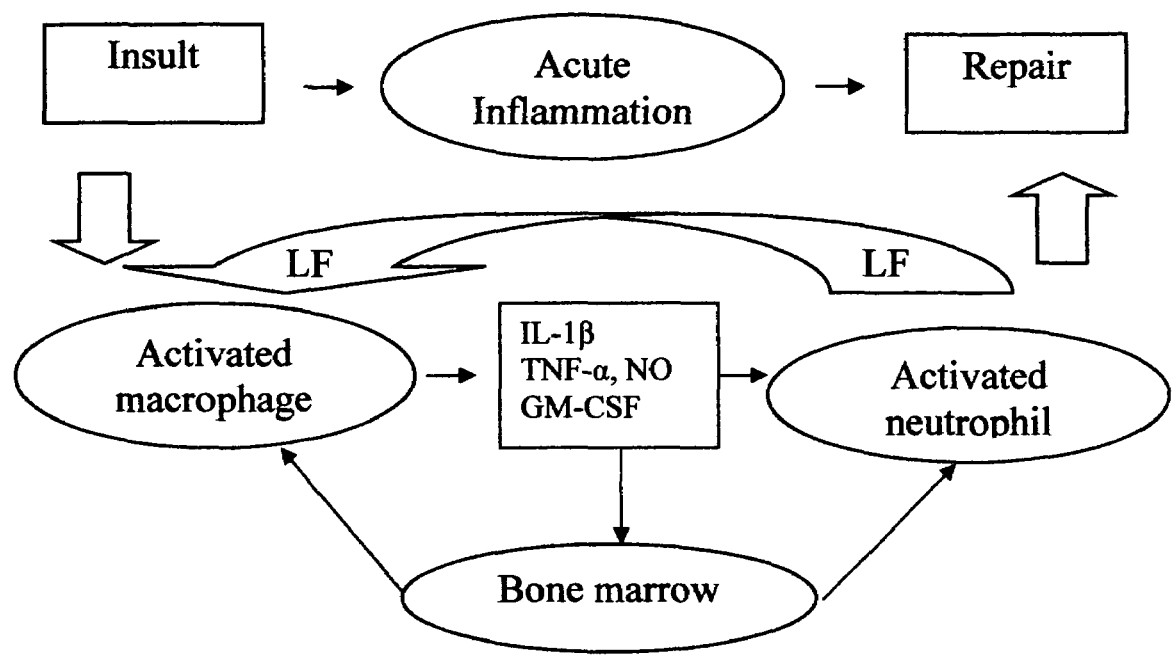
FIG. 1 Illustrates molecular events during development of acute inflammation.
Figure 2:
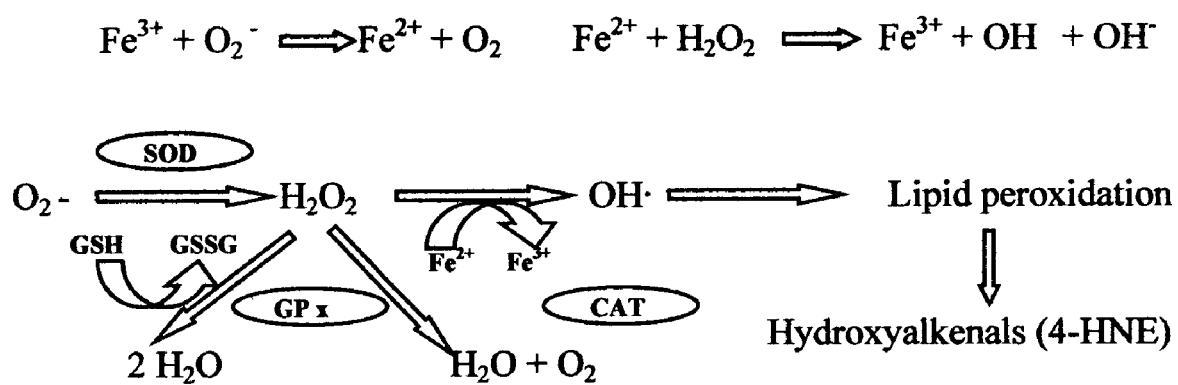
FIG. 2 Illustrates cellular mechanisms of iron-dependent ROS generation.

Table 1. Illustrates a composition of bovine milk lactoferrin.

Table 2. Illustrates clinical data relevant to lactoferrin treated Alzheimer's patients.

DESCRIPTION OF THE PREFERRED EMBODIMENTS

According to the present invention exogenous lactoferrin is used to modulate the molecular events during development of many age-related disorders, including autoimmune, neurodegenerative and immune hypersensitivity disorders in humans. In particular, lactoferrin is used to reduce the levels of intracellular ROS which in turn can influence a cell cycle and specifically apoptosis. Apoptosis is a programmed cells death, characterized by activation of caspases. There are two pathways of caspase activation: 1) the cell surface death receptor pathway, activation of caspase-8 recruits death-inducing signaling complex, which is the critical event that transmits the death signal. Activated caspase-8 can activate downstream caspases by direct cleavage or indirectly by cleaving Bid and inducing cytochrome c release from the mitochondria. 2) the mitochondria-initiated pathway, in which caspase activation is triggered by the formation of a multimeric Apaf-1/cytochrome c complex that is fully functional in recruiting and activating procaspase-9. Activated caspase-9 will then cleave and activate downstream caspases such as caspase-3, -6, and -7. This pathway is regulated at several steps, including the release of cytochrome c from the mitochondria, the binding and hydrolysis of dATP/ATP by Apaf-1. Thus lactoferrin is used to control primarily the cell cycle and apoptosis.

Also, according to the present invention exogenous lactoferrin is used to modulate the Th1/Th2 balance in the context of immune homeostasis. In particular, lactoferrin is used to control oxidative stress-induced immune imbalance in humans and other animals. Although, many pathological phenomena have been correlated with ROS, the role of oxidative stress in such chronic disorder-related decline or increase of T-cell activity is not yet clear. Still, according to the present invention lactoferrin is used to counterbalance allergen-reactive Th2 responses, also known as type 1 hypersensitivity (immediate) including allergy.

The present invention is based on the observation of clinical results obtained from both large patient population and individual cases utilizing common clinical regimen, followed by physician evaluation. In all examples of administration of lactoferrin in the treatment of autoimmune and/or neurologic conditions, lactoferrin was found effective, specifically including the prevention and slowing down of the progression of the disease. According to the present invention lactoferrin is also used to restore and maintain central nervous system health. The present invention has broad implications in the alleviation, treatment, or prevention of many age-related disorders including chronic autoimmune, neurodegenerative or immune hypersensitivity (allergy) disorders, which are exemplified hereto:

Allergy. Allergy is defined as a hypersensitivity of the body's immune system in response to exposure to antigens, such as foods, pollen, dust, or certain drugs. A severe form of allergy is called anaphylactic shock, which is considered as a medical emergency. Symptoms of allergy are various and may include skin rashes, swelling, and difficulties to breathing. Symptoms of anaphylactic shock may include dizziness, loss of consiousness, swelling of the tongue and breathing tubes, blueness of the skin, low blood pressure, and death.

Multiple sclerosis (MS). MS is a disease of the central nervous system identifiably by progressive symptoms, and pathologically by scattered areas of demyelination affecting the brain, spinal cord and optic nerves. Generally, individuals note the first signs between the ages of 15 and 50. Affected patients encounter bouts of inflammatory demyelination producing the classic course of the disease of exacerbation—remittance.

Lupus. Lupus is a chronic inflammatory disease of uncertain origin, affecting many systems of the body, characterized by a rash on the face and other areas exposed to sunlight, involving the vascular and connective tissues of many organs, and accompanied by serologic abnormalities. Lupus is a chronic (long-lasting) autoimmune disease where the immune system, for unknown reasons, becomes hyperactive and attacks normal tissue.

Amyotrophic lateral sclerosis (ALS). ALS, also known as Lou Gehrig's disease, is a progressive disease of the nervous system. ALS attacks motor neurons, which are among the largest of all nerve cells in the brain and spinal cord. These cells send messages to muscles throughout the body. In ALS, motor neurons die and the muscles do not receive these messages. As a result, muscles weaken as they lose their ability to move. Eventually, most muscle action is affected, including those which control swallowing and breathing, as well as major muscles in the arms, legs, back and neck. There is, however, no loss of sensory nerves, so people with ALS retain their sense of feeling, sight, hearing, smell and taste. According to the National Institutes of Health, some 4,600 people in the United States are newly diagnosed with ALS each year.

Chronic Fatigue Syndrome (CFS). CFS is a condition of prolonged and severe tiredness or fatigue that is not relieved by rest and is not directly caused by other conditions. The exact cause of chronic fatigue syndrome is unknown. Some researchers suspect it may be caused by a virus, such as human herpes virus-6 (HHV-6). However, no distinct viral cause has been identified. Recent studies have shown that chronic fatigue syndrome may be caused by nonspecific inflammation in the nervous system; and that this may trigger some sort of autoimmune process. Other factors such as age, prior illness, stress, environment, or genetic disposition may also play a role. Symptoms of CFS are similar to those of most common viral infections (muscle aches, headache, and fatigue), often developing within a few hours or days and lasting for several months or more. Although common fatigue is different from CFS, both are oxidative stress-driven disorders.

Rheumatoid arthritis (RA). RA is a systemic autoimmune disease which initially attacks the synovium, a connective tissue membrane that lines the cavity between joints and secretes a lubricating fluid. The cause of rheumatoid arthritis is unknown. In fact, it is possible that there is no single cause of RA. Infectious, genetic, and hormonal factors may play a role. The disease can occur at any age, but the peak incidence of disease onset is between the ages of 25 and 55. The incidence increases with age. The onset of the disease is usually gradual, with fatigue, morning stiffness lasting more than one hour, diffuse muscular aches, loss of appetite, and weakness. Eventually, joint pain appears, with warmth, swelling, tenderness, and stiffness of the joint after inactivity.

Alzheimer's Disease (AD). AD is a neurodegenerative disorder mainly characterized by the progressive and irreversible loss of nerve cells (neurons) located in a specific brain area, the hippocampus. AD is a disease that attacks the brain and results in impaired memory, thinking and behavior. The destruction of nerve cells leads to a decrease in neurotransmitters. The correct balance of neurotransmitters is critical to the brain. Three neurotransmitters commonly affected by AD are acetylcholine, serotonin, and norepinephrine. Memory impairment is a necessary feature for the diagnosis. Change in one of the following areas must also be present: language, decision-making ability, judgment, attention, and other related areas of cognitive function and personality. Alzheimer's disease (AD) is a slowly progressive form of dementia.

Parkinson's Disease (PD). PD is a degenerative disease that often manifests itself late in life and is marked by abrupt motions, muscle tremors and a peculiar gait. People who suffer from this disease, once thought to be strictly neuromuscular, lose neurons from a part of the brain called the substantia nigra that produces the neurotransmitter dopamine, which helps brain cells communicate with one another. Parkinson's patients also experience a slowing of some cognitive functions and have difficulty with complex tasks.

Hantington's Disease (HD). HD is a genetic disease involving the degeneration of nervous system cells, including brain cells, beginning at around age 30. HD is characterized initially by bradykinesia and rigidity then choreiform movements.

Creutzfeldt-Jakob Disease (CJD). CJD, human transmissible spongiform encephalopathies have been transmitted to primates and to other animals through cell-free injections of infected brain tissue. Spongiform encephalopathies occur in several mammalian species. Scrapie affects sheep, and bovine spongiform encephalopathy or mad cow disease occurs primarily in cows. Kuru, which affects humans, is associated with cannibalism in New Guinea natives. C-J syndrome and Gerstmann-Straussler-Schenker syndrome, which affect humans, appear to occur through both genetic and infectious routes, as known for scrapie. The infectious agent has been characterized and is resistant to inactivation by ultraviolet radiation, formalin, heat and enzymes which denature nucleic acids. It can be inactivated (i.e. its infectivity destroyed) by proteases and other treatments that denature proteins.

Stroke. Stroke is a cardiovascular disease that affects the blood vessels supplying blood to the brain. It is also sometimes called brain attack. A stroke occurs when a blood vessel bringing oxygen and nutrients to the brain bursts or is clogged by a blood clot or some other particle. Deprived of oxygen, nerve cells in the affected area of the brain can't function and die within minutes. And when nerve cells can't function, the part of the body controlled by these cells can't function either. There are four main types of stroke: two caused by blood clots or other particles, and two by hemorrhage. Cerebral thrombosis and cerebral embolism are by far the most common, accounting for about 70-80 percent of all strokes. They're caused by clots or particles that plug an artery. Cerebral and subarachnoid hemorrhages are caused by ruptured blood vessels. They have a much higher fatality rate than strokes caused by clots.

Cancer. Cancer is defined as an uncontrolled growth of abnormal cells which have mutated from normal tissues. Cancer can kill when these cells prevent normal function of affected vital organs or spread throughout the body to damage other key systems. There are at least 200 different kinds of cancers, which can develop in almost any organ. Typically, the growth of cells in the body is strictly controlled—new cells are made as needed to replace older ones or to perform needed functions. If the balance of cell growth and death is disturbed, cancer may occur. Problems in the regulation of cell growth can be caused by abnormalities of the immune system, which normally would detect and stop aberrant growth. Other potential causes of cancer include radiation, sunlight, tobacco, certain viruses, benzene, certain poisonous mushrooms, and aflatoxins amongst many others.

According to the present invention, the lactoferrin used may be human lactoferrin, either natural or recombinant, or bovine milk lactoferrin (BLF). A preferred lactoferrin is bovine milk lactoferrin, which may be obtained as partially iron saturated form (typically 10%-25% metal loading) from commercial sources, including DMV International Nutritionals, Frasier, N.Y.; Glanbia Foods, Inc., Richfield, Id.; Tatua Nutritonals, New Zealand: or Morinaga Milk Industry Co., Ltd., Japan. The characteristics of such preferred lactoferrin is presented in Example 1, only for the purpose of illustration.

A human recombinant lactoferrin which may be used is described in U.S. Pat. No. 6,066,469, U.S. Pat. No. 6,277,817 B1, and U.S. Pat. No. 6,455,687 B2, all of which are incorporated herein by reference.

Lactoferrin is administered in accordance with the present invention either enteraly, preferably orally, in the form of a powder, aqueous or non-aqueous solution or gel, or parenterally, preferably intravenously, in the form of an injectable solution, as an aid to treat the symptoms of the above-identified disorders. Preferable formulations or medicaments of the present invention comprise lactoferrin alone or in combination with pharmaceutical or nutritional carriers such as, water, saline, starch, maltodextrin, pullulan, silica, talcum, stearic acid, its magnesium or calcium salt, polyethyleneglycol, arabic, xanthan or locoust bean gums and fatty emulsions and suspensions that will be readily apparent to the skilled artisan. The lactoferrin is preferably present in the formulation at a level of 0.1 milligram to 500 milligram, more preferably between 1 to 100 milligram, based on 1 milliliter or 1 gram of the carrier. An effective amount of lactoferrin varies depending on the individual treated, severity of the neurodegenerative or autoimmune disorder and the form of administration. Preferable in treating individual, a single or twice daily dose of 0.01 milligram to 20 milligrams, more preferable 0.1 milligram to 2 milligram of lactoferrin per kilogram of body weight is administrated. Lactoferrin can also be delivered as a liposomal formulation, including transdermal patches.

According to the present invention, lactoferrin can be incorporated in formulation with any drug adjuvant therapy and delivered alone or simultaneously per os, intravenously, intraperitonealy, intraarterialy, intramascularly, subcutanoeusly, transdermally, or as an intranasal spray, or intrabroncheal inhalation mist, at the effective concentration ranges set forth herein above. Preferred formulations or medicaments of the present invention comprise incorporating the lactoferrin into a chewable tablet as illustrated in Example 2.

Example 1

Bovine Milk Lactoferrin (BLF)

Figure 3:
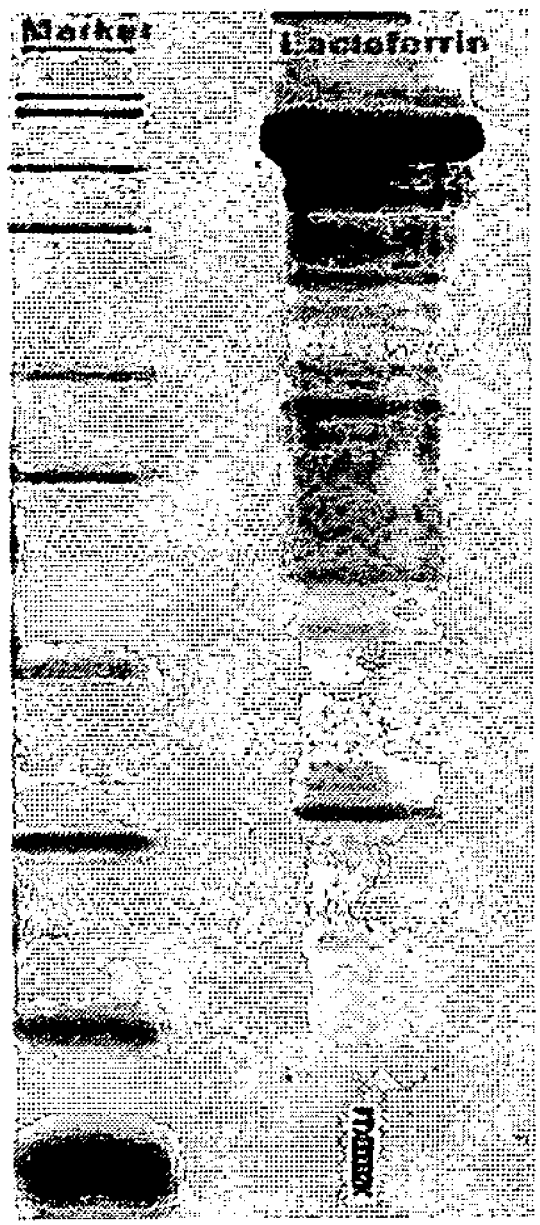
FIG. 3 Illustrates SDS PAGE separation of bovine milk lactoferrin (right), along with a molecular weight standard proteins (left).

Bovine milk lactoferrin is a highly purified lyophilized powder derived from cows milk. It is at least 80% pure (as per 1D SDS PAGE) and contains at least 90% (w/w) of protein and peptides (Table 1). A typical preparation of BLF shows a major band in 1D SDS PAGE corresponding to a molecular weight at 80 kDa (FIG. 3). BLF is free of Coliform bacteria, *Salmonella* and pathogenic *Staphylococcus*. BLF it is not toxic for animals when orally administered at 2 g/kg/day for several weeks.

Example 2

Lactoferrin Chewable Tablets

Tablets are made from the following powdered ingredients, mixed in a commercial mixer 95.45 parts dextrose; 2.97 parts BLF; 0.6 part citric acid; 0.34 part orange flavor; 0.07 part orange color, and mixed for 10 minutes. Then, 0.53 part of calcium stearate is added for additional 5 minutes of mixing. Each of the procedures should be performed with precautions against exposure to the powders and dusts that are formed, and particularly against their inhalation. The tablets (25 mg of BLF per tablet) are formed by direct compression with 4,000 pounds to obtain hardness of ~180 Newtons, a characteristic of chewable tablets.

Example 3

Lactoferrin Reduces Apoptosis

Apoptosis can be measured in U937 cells maintained in RPMI1640 (GIBCO-Invitrogen, Inc.) medium. The growth medium is supplemented with 10% FBS (Sigma-Aldrich Inc), glutamine (292 mg/L), penicillin (100 U/ml) and streptomycin (100 µg/ml). Cells are pre-treated with lactoferrin (125 or 250 µg/ml) or N-acetyl-L-cysteine (as control; 10 mM) for 3 h at 37° C. in a humified 5% $CO_2$ atmosphere. Pretreated cells are exposed to glucose oxidase (GO) (500 ng per ml: this concentration killed cells via apoptosis, determined in preliminary studies) and activation of caspase 3 is determined calorimetrically. Briefly, cells (0, 1, 3, 6, 9, 12, and 18 h post-treatment with GO (500 ng per ml), are collected by centrifugation (1,000 rpm, at 4° C., for 10 min). The pellets are lysed in ice-cold lysis buffer and clarified by centrifugation (14,000 rpm, at 4° C., for 15 min). Enzymatic reactions are carried out in 96-well plates after addition of cell supernatant, reaction buffer and appropriate caspase substrate. Caspase activity is determined by measuring the change in absorbance at 405 nm. Accordingly, lactoferrin reduced apoptosis by 80%.

To further characterize apoptosis, flow cytometric analysis is performed on cells treated with lactoferrin, GO and their combination after AnnexinV-FITC staining. z-DEVD-fmk (N-benzyloxycarbonyl-Asp(OMe)-Glu(OMe)-Val-Asp (OMe)-fluoro-methylketone) a caspase –3 inhibitor was used as control. Cells are stained with Annexin V-FITC (Becton Dickinson) and analyzed on a FACScan flow cytometer. Again, lactoferrin reduced apoptosis by 80%.

Example 4

Lactoferrin Reduces Immune Hypersensitivity

To determine whether pollen has an impact on intracellular ROS and whether lactoferrin can modulate such impact, both partially and fully saturated lactoferrins are used in various in vitro and in vivo experiments, including measurement of ROS in A549 cell line. Briefly, cells are pre-treated with LF or NAC (as control; 10 mM) for 3 h. Pretreated cells are "loaded" with 2',7'-dichlorodihydro-fluorescein diacetate (H2DCF-DA; Molecular Probes Eugene, Oreg.) at 5 µM final concentration for 15 min, at 37° C. Pre-treated, H2DCF-DA-loaded cells are exposed to pollen (ragweed), pollen with partially or fully iron saturated lactoferrins, glucose oxidase (positive control) or PBS. Changes in fluorescence intensity in mock- and treated cells were determined with Flx-800 microplate fluorescence reader (Bio-Tek, Inc.) at excitation/emission wavelengths of 485/528 nm. Statistically significant difference in reduction of ROS levels is observed for partially iron saturated lactoferrin ("like" apo-lactoferrin) not fully iron saturated lactoferrin (holo-lactoferrin).

Treatment of Autoimmune Disorders

Figure 4:
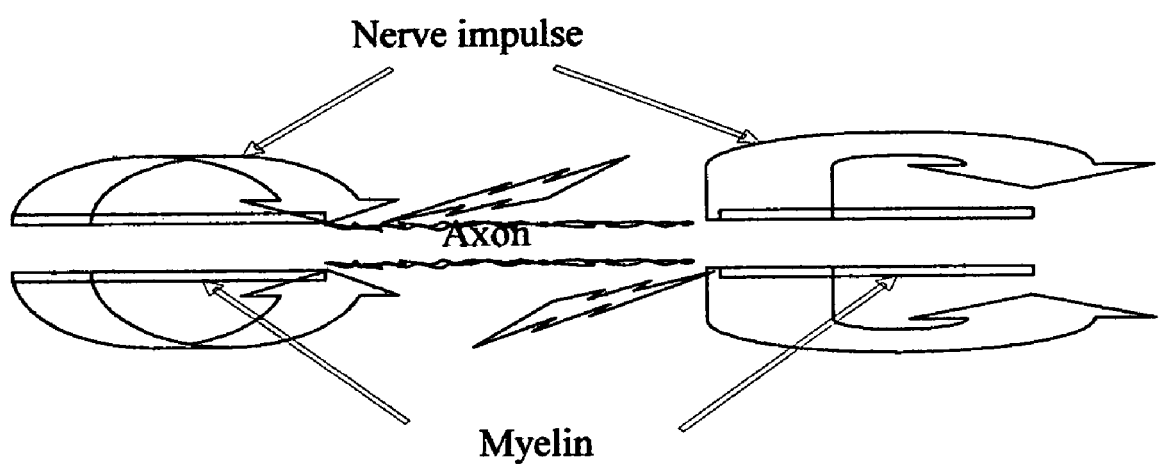
FIG. 4 Illustrates a schematic presentation of pulse conduction in axon.

According to the present invention, exogenous lactoferrin is used to modulate the molecular events during development of autoimmune disorders in humans. In a preferred embodiment of the present invention, lactoferrin is used for treatment of multiple sclerosis. MS is the autoimmune disorder. There is growing evidence suggesting that autoimmune T cell responses to myelin basic protein (MBP) are engaged in the pathogenesis of MS. MS is characterized by disseminated patches of demyelination in the brain and spinal cord, resulting in multiple and varied neurologic symptoms. The myelin sheath, a lipid-rich membrane, both insulates and enhances conduction in nerve axons. Nerves can only conduct pulses of energy efficiently if covered by myelin (FIG. 4).

This process of demyelination usually starts in adolescence, but the first symptoms may not be experienced until the early to mid-twenties—this is when the diagnosis is usually made. So the affected person is asymptomatic for years, in spite of the development of lesions, because nerve conduction can still occur in spite of large areas of demyelination. Studies with NMR (Nuclear Magnetic Resonance) have permitted researchers to observe the appearance of lesions days before the appearance of symptoms during a period of exacerbation, and the disappearance of these fresh plaques during the period of remission that follows. The exact mechanism(s) of demyelination in multiple sclerosis is still unresolved, both antigen-specific and—non-specific events having the potential to generate the myelinolytic process.

The effectiveness of lactoferrin in the treatment of multiple sclerosis is illustrated in Example 5 and 6.

Example 5

MS—Large Population Clinical Studies

In our placebo controlled clinical trial, LF was administered to patients orally, twice daily (25 mg/dose), for seven consecutive days. Six of the patients suffer from MS and 24 were diagnosed with persistent fatigue. Blood samples were taken on 1 day before treatment, 1 day, and 7 days after cessation of the treatment. The leukocytes were isolated from the whole blood, the cultures were established and cells stimulated with phytoheamoglutinin (PHA) and lipopolysaccharide (LPS) overnight. In the plasma the following parameters were measured: endogenous lactoferrin, NO and cortisol. In the unstimulated and stimulated cell cultures the activities of IFN gamma, TNF alpha, IL-6, and IL-10 were determined. In addition, the blood smears were stained and the percentage of main cell types was determined.

The production of IL-10 was increased in MS patients treated with lactoferrin by 8.13× on average (individual increases: 10×; 32×; 4×; 17×; 7×). On the other hand in the placebo group, IL-10 activity dropped by 34%. The dramatic increase in the IL-10 production, was associated with changes in IFN gamma production, which dropped on average by 4× in MS patients treated with lactoferrin (from 186 pg/ml to 46 pg/ml). The stimulation was observed in only one MS patient. In the placebo group the changes in the production of IFN gamma were minor. Elevation of serum cortisol would be advantageous in diminishing manifestations of MS. In fact, our clinical studies showed that cortisol has been increased in all MS patients treated with lactoferrin. In placebo group, the level of cortisol dropped by 14%. More important the changes in the immunological parameters were correlated with improvement of overall wellness and complete release from common fatigue.

Example 6

MS Individual Treatment

Lactoferrin tablets (Example 2) were administered twice daily for 12 months to an adult woman (42 years old) with a history of disseminated sclerosis (subject A). The patient was evaluated three times: at the initiation, 6 months into the therapy and 11 months after initiation of the treatment, by using NMR imaging analysis. At the initiation of therapy, subject A experienced difficulties with walking and performing routine daily exercises. NMR analysis showed significant demyelination by number of hyper intensive centers in both brain and spinal cord. Six months into the therapy subject A was able to walk and perform most of daily duties. The NMR showed less hyper intensive centers in brain. After the treatment, subject A reported no limitation on daily duties and exercises and the NMR confirmed less lesions in brain and spinal cord. The rate of demeylination was significantly reduced in subject A after one year lactoferrin treatment.

Example 7

RT Treatment

Lactoferrin tablets (Example 2) were self-administered by subject B, an adult woman with a long history of rheumatoid arthritis. Tenderness in all active joints and deformities in fingers, wrists and elbows were very visible signs of inflammation. Over several years subject B had experienced no relief from medications prescribed by physicians. Pain relief was observed as soon as a regime was initiated in which two tablets of lactoferrin were taken orally each day. Over three months the morning stiffness of joints improved to the point at which symptoms were absent. Also, joints deformities, especially those on fingers, were significantly reduced.

Example 8

CFS Treatment

Lactoferrin tablets (Example 2) were self-administered by subject C, an adult male with a history of persistent fatigue. In general, subject C reported fluctuating level of energy from time to time. Also, tiredness and muscle weakness renders subject C incapable of normal activities of daily living. Over several months subject C had experienced no relief from over the counter medications. After six day treatment with 2 tablets a day, subject C reported increased level of energy and no muscle weakness. Within 2 weeks into treatment subject C declared free of any symptoms previously described as fatigue.

These data demonstrate that lactoferrin given orally in the range of 25-150 mg daily, is an effective and safe treatment to alleviate the symptoms of autoimmune disorders, in particular multiple sclerosis, rheumatoid arthritis and CFS in humans.

Treatment of Neurodegenerative Disorders

According to the present invention, exogenous lactoferrin is used to modulate the molecular events during development of neurodegenerative disorders in humans. In another preferred embodiment of the present invention, lactoferrin is used for treatment of Alzheimer's disease. AD is slowly progressive neurodegenerative disorder, with a mean survival interval of 9 to 10 years following onset. The first symptoms of AD often include memory loss, temporal and geographical disorientation, and language deficits. As the disease progresses, these deficits become more severe and personality changes are common, including withdrawal from social settings and impairments in judgement and problem solving. Sensory, motor, and primary visual functions are typically not lost until the final stages of the disease. The two pathognomonic lesions of Alzheimer's disease are senile plaques (SPs) and neurofibrillary tangles (NFTs). In addition to SPs and NFTs, the most prominent feature of AD pathology is massive neuronal loss, primarily in the hippocampus. Neurofibrillary tangles are intraneuronal lesions composed primarily of the microtubule-associated protein tau. The major constituents of senile plaques are amyloid fibrils made of 39-43 amino acid amyloid-β(Aβ) peptides. There are two types of senile plaques: neuritic plaques, which are surrounded by dystrophic neurites and diffuse plaques, which are not accompanied by abnormal neurites. The neuritic and diffuse plaques may contain different populations of Aβ peptides. The neuritic plaques contain mostly A β42, whereas diffuse plaques are made of A β40. Although very little is known about the mechanisms by which these different types of senile plaques are generated, the presence of A β40 and A β42 in the CSF of normal and AD patients suggests that Aβ is constitutively produced and secreted in vivo.

The effectiveness of lactoferrin in the treatment of the neurodegenerative disorders is illustrated in the following Examples:

Example 9

AD Treatment

Lactoferrin tablets (Example 2) were administered twice daily for 3 months to a 61 year old male with a history of increasing memory problems and lack of focus (subject D). The patient was diagnosed with a moderate Alzheimer's disease. The effectiveness of lactoferrin treatment was evaluated two times following the initial diagnose: 1 month into the therapy and 2 months after initiation of the treatment, by using standard psychological tests, including Mini Mental State Examination (MMSE). A transient occurrence of excitement was reported by subject D during first week of treatment. An improvement in memorizing daily activities was reported after two weeks of treatment, followed by further revitalization as shown in table 2.

A continuous regression (improvement) in dementia has been reported by subject D for one year now.

Example 10

Stroke/TIA Treatment

Lactoferrin tablets (Example 2) were self-administered by subject E, an adult woman suffering from the transient ischemic attack (TIA). Lactoferrin tablets were administered orally immediately after experiencing numbness in right hand, difficulties to walk and slurred speech. Following administration of first tablet, subject E reported immediate occurrence of excitement in the experience of relief from the numbness. Further improvement in walking and articulate speech was noticed within 15 minutes following an initial attack. Subject E continued self-administration of lactoferrin tablets twice daily for 1 month and did not report reoccurrence of TIA or stroke for 3 years.

These data demonstrate that lactoferrin given orally in the range of 25-150 mg daily, is an effective and safe treatment to alleviate the symptoms of neurodegenerative disorders, in particular AD and stroke in humans.

It is understood that the examples and embodiments described herein are for illustrative purposes only and that various modifications or changes in light thereof will be suggested to persons skilled in the art and are to be included within the spirit and purview of this application and scope of the appended claims.

What we claimed is:

1. A method for the treatment of multiple sclerosis comprising administering to a patient having said multiple sclerosis an effective amount of lactoferrin.

2. The method of claim 1 wherein said multiple sclerosis is accelerated by oxidative stress-induced apoptosis.

3. The method of claim 1 wherein said multiple sclerosis is accelerated by Th1/Th2 imbalance.

4. The method of claim 1 wherein said lactoferrin is bovine milk lactoferrin.

5. The method of claim 1 wherein said lactoferrin is partially iron saturated.

6. The method of claim 1 wherein said lactoferrin is administered as a pharmaceutical or nutritional composition in admixture with an acceptable carrier.

7. A method for attenuating demyelination in a subject having said multiple sclerosis, said method comprising administering to said subject an effective amount of partially iron saturated lactoferrin, in a pharmaceutically or nutritionally acceptable carrier.

* * * * *